US011915830B2

(12) United States Patent
Goltra et al.

(10) Patent No.: US 11,915,830 B2
(45) Date of Patent: *Feb. 27, 2024

(54) INTELLIGENT PROMPTING OF PROTOCOLS

(71) Applicant: MEDICOMP SYSTEMS, INC., Chantilly, VA (US)

(72) Inventors: Peter S. Goltra, Middleburg, VA (US); Daniel A. Gainer, Shenandoah Junction, WV (US)

(73) Assignee: MEDICOMP SYSTEMS, INC., Chantilly, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/942,287

(22) Filed: Sep. 12, 2022

(65) Prior Publication Data

US 2023/0113333 A1 Apr. 13, 2023

Related U.S. Application Data

(63) Continuation of application No. 16/774,236, filed on Jan. 28, 2020, now Pat. No. 11,476,001, which is a
(Continued)

(51) Int. Cl.
*G16H 50/30* (2018.01)
*G06F 16/2457* (2019.01)
(Continued)

(52) U.S. Cl.
CPC ....... *G16H 50/30* (2018.01); *G06F 16/24578* (2019.01); *G16H 10/60* (2018.01); *G16H 70/20* (2018.01)

(58) Field of Classification Search
CPC ........ G16H 50/30; G16H 10/60; G16H 70/20; G06F 16/24578
See application file for complete search history.

(56) References Cited

U.S. PATENT DOCUMENTS 5,262,943 A 11/1993 Thibado et al.
5,387,164 A 2/1995 Brown, Jr.
(Continued)

FOREIGN PATENT DOCUMENTS

GB 2389290 A 12/2003
WO 0060496 A3 2/2001
(Continued)

OTHER PUBLICATIONS

Slain, T; S.Rickard-Aasen; J.Pringle; G.G.Hegde; J.Shang; W.Johnjulio; A.Venkat. An Operational Analysis of Integrating Screening and Brief Intervention into the Normal Workflow of the Emergency Department Without Additional Resources. Annals of Emergency Medicine vol. 62, Issue 4, Supplement. (Year: 2013).*
(Continued)

*Primary Examiner* — Linh Giang Le
(74) *Attorney, Agent, or Firm* — Merchant & Gould P.C.

(57) ABSTRACT

A method of generating a user interface for use in documenting a patient encounter comprises: automatically identifying, with a computing device, at least one documentation protocol based on at least one element of the patient's medical record; and generating a user interface including at least one of the identified documentation protocols, the at least one identified documentation protocol identifying at least one medical finding. A system comprises a data store encoded on a memory device, the data store comprising documentation protocols. The system further comprises an input apparatus. A computing device is in data communication with the data store and the input apparatus. The computing device is programmed to receive findings input through the input apparatus, identify a documentation protocol based on the finding input through the input apparatus, and generate a user interface. The user interface comprising the identified documentation protocol.

12 Claims, 13 Drawing Sheets

Related U.S. Application Data continuation of application No. 14/629,215, filed on Feb. 23, 2015, now Pat. No. 10,600,505.

(60) Provisional application No. 61/943,252, filed on Feb. 21, 2014.

(51) Int. Cl.
  *G16H 10/60* (2018.01)
  *G16H 70/20* (2018.01)

(56) References Cited

U.S. PATENT DOCUMENTS

| | | |
|---|---|---|
| 5,453,009 A | 9/1995 | Feldman |
| 5,784,504 A | 7/1998 | Anderson et al. |
| 5,924,074 A | 7/1999 | Evans |
| 6,265,010 B1 | 7/2001 | Barbara et al. |
| 6,639,584 B1 | 10/2003 | Li |
| 7,133,937 B2 | 11/2006 | Leavitt |
| 7,499,862 B1 | 3/2009 | Bangalore et al. |
| 7,801,740 B1 | 9/2010 | Lesser |
| 2002/0004729 A1 | 1/2002 | Zak et al. |
| 2003/0069759 A1 | 4/2003 | Smith |
| 2004/0006057 A1 | 12/2004 | Dahlin et al. |
| 2005/0144039 A1 | 6/2005 | Tamblyn et al. |
| 2005/0273363 A1 | 12/2005 | Lipscher et al. |
| 2006/0007189 A1 | 1/2006 | Gaines et al. |
| 2006/0026536 A1 | 2/2006 | Hotelling et al. |
| 2006/0041450 A1 | 2/2006 | Dugan |
| 2006/0080140 A1 | 4/2006 | Buttner et al. |
| 2006/0197750 A1 | 9/2006 | Kerr et al. |
| 2006/0206361 A1 | 9/2006 | Logan |
| 2006/0241977 A1 | 10/2006 | Fitzgerald et al. |
| 2007/0088525 A1 | 4/2007 | Follades et al. |
| 2007/0118400 A1 | 5/2007 | Morita et al. |
| 2007/0165049 A1 | 7/2007 | Syed et al. |
| 2007/0185390 A1 | 8/2007 | Perkins et al. |
| 2007/0239488 A1 | 10/2007 | Derosso |
| 2008/0040161 A1 | 2/2008 | Faux et al. |
| 2008/0120578 A1 | 5/2008 | Kariathungal et al. |
| 2008/0122796 A1 | 5/2008 | Tolmasky et al. |
| 2008/0168403 A1 | 7/2008 | Westerman et al. |
| 2008/0198514 A1 | 8/2008 | Jogo |
| 2008/0208631 A1 | 8/2008 | Morita et al. |
| 2008/0228529 A1 | 9/2008 | Willson et al. |
| 2009/0018867 A1 | 1/2009 | Reiner |
| 2009/0021475 A1 | 1/2009 | Steinle et al. |
| 2009/0024411 A1 | 1/2009 | Albro et al. |
| 2009/0265185 A1 | 10/2009 | Finn et al. |
| 2010/0094657 A1 | 4/2010 | Stern et al. |
| 2010/0131883 A1 | 5/2010 | Linthicum et al. |
| 2010/0137693 A1 | 6/2010 | Porras et al. |
| 2010/0194976 A1 | 8/2010 | Smith et al. |
| 2011/0004847 A1 | 1/2011 | Herrold et al. |
| 2011/0054944 A1 | 3/2011 | Sandberg et al. |
| 2011/0078570 A1 | 3/2011 | Larsen et al. |
| 2011/0178819 A1 | 7/2011 | Mchorney |
| 2011/0306926 A1 | 12/2011 | Woo |
| 2012/0004932 A1 | 1/2012 | Sorkey et al. |
| 2013/0073316 A1* | 3/2013 | Miglietta ............... G16H 70/60 705/3 |
| 2016/0203277 A1 | 7/2016 | Okabe et al. |

FOREIGN PATENT DOCUMENTS

| | | | |
|---|---|---|---|
| WO | WO-0060496 A3 * | 2/2001 | ........... G06F 16/258 |
| WO | 0180117 A1 | 10/2001 | |
| WO | 2004008273 A2 | 1/2004 | |

OTHER PUBLICATIONS

Wyatt, Jeremy C; Altman, Douglas G; Heathfield, Heather A, Pantin, Charles F A. "Development of design—a—trial, a knowledge based critiquing system for authors of clinical trial protocols." Computer Methods and Programs in Biomedicine . 43.3-4 : 283-291. (1994) (Year 1994).

International Search Report and Written Opinion for Application No. PCT / US15 / 17133 dated Jun. 16, 2015.

Willis et al., Tablet PC's as Instructional Tools or the Pen is mightier than the "Board". Oct. 28-30, 2004, 153-159 pages, SIGITE '04, ACM.

Dean Rubine. "Combining Gestures and Direct Manipulation", 1992, 659-660 pages, CHI '92.

International Search Report and Written Opinion for PCT / US2010/ 038878, dated Jul. 27, 2012.

Conway, Jason D., et al. "Endoscopic electronic medical record systems." Gastrointestinal endoscopy 67.4 (2008) 590-594.

\* cited by examiner

290

| Protocol: Congestive Heart Failure | | |
|---|---|---|
| Protocol ID: 1 | | |
| Medical Findings | | |
| Type | ID | Description |
| Symptoms | 100003 | Dyspnea |
| Symptoms | 100015 | Fatigue |
| ... | | |
| History | 200010 | Congestive Heart Failure |
| ... | | |
| Examination | 300024 | Jugular Venous Distension |
| Examination | 300011 | Rales |
| Examination | 300008 | Peripheral Edema |
| ... | | |
| Tests | 400075 | EKG |
| Tests | 400262 | CBC |
| Tests | 400321 | Troponin |
| Tests | 400400 | CPK - MB |
| Tests | 400488 | Renal Function Panel |
| Tests | 400511 | CXR |
| ... | | |
| Diagnoses | 500400 | Congestive Heart Failure |
| ... | | |
| Therapy | 600001 | Admission to Emergency Department |
| Therapy | 600011 | Medication Reconciliation |
| Therapy | 600026 | Medication Compliance |
| Therapy | 600142 | Diuretics |
| Therapy | 600199 | Blood Pressure Control |

| | Protocol: Bacterial Pneumonia<br>Protocol ID: 2 | |
|---|---|---|
| Medical Findings | | |
| Type | ID | Description |
| Symptoms | 100003 | Dyspnea |
| Symptoms | 100014 | Productive Cough |
| Symptoms | 100050 | Shaking Chills |
| Symptoms | 100091 | Confusion |
| ... | | |
| Examination | 300063 | Tachycardia |
| Examination | 300079 | Increased Respiratory Rate |
| Examination | 300091 | Confusion |
| Examination | 300102 | Blue Lips |
| Examination | 300105 | Decreased Breath Sounds |
| ... | | |
| Tests | 400201 | Pulse Oximetry |
| Tests | 400511 | CXR |
| Tests | 400262 | CBC |
| ... | | |
| Diagnoses | 500005 | Bacterial Pneumonia |
| ... | | |
| Therapy | 600011 | Medication Reconciliation |
| Therapy | 600045 | Oxygen |
| Therapy | 600188 | Antibiotics |

| | Merged Protocol | |
|---|---|---|
| Medical Findings | | |
| Type | ID | Description |
| Symptoms | 100003 | Dyspnea |
| Symptoms | 100015 | Fatigue |
| Symptoms | 100014 | Productive Cough |
| Symptoms | 100050 | Shaking Chills |
| Symptoms | 100091 | Confusion |
| . . . | | |
| History | 200010 | Congestive Heart Failure |
| . . . | | |
| Examination | 300063 | Tachycardia |
| Examination | 300079 | Increased Respiratory Rate |
| Examination | 300091 | Confusion |
| Examination | 300102 | Blue Lips |
| Examination | 300024 | Jugular Venous Distension |
| Examination | 300105 | Decreased Breath Sounds |
| Examination | 300011 | Rales |
| Examination | 300008 | Peripheral Edema |
| . . . | | |
| Tests | 400201 | Pulse Oximetry |
| Tests | 400075 | EKG |
| Tests | 400262 | CBC |
| Tests | 400321 | Troponin |
| Tests | 400400 | CPK - MB |
| Tests | 400488 | Renal Function Panel |
| Tests | 400511 | CXR |
| . . . | | |
| Diagnoses | 500005 | Bacterial Pneumonia |
| Diagnoses | 500400 | Congestive Heart Failure |
| . . . | | |
| Therapy | 600001 | Admission to Emergency Department |
| Therapy | 600011 | Medication Reconciliation |
| Therapy | 600026 | Medication Compliance |
| Therapy | 600045 | Oxygen |
| Therapy | 600142 | Diuretics |
| Therapy | 600199 | Blood Pressure Control |
| Therapy | 600188 | Antibiotics |

| | Protocol: Congestive Heart Failure Re-admission | |
|---|---|---|
| | Protocol ID: 3 | |
| Medical Findings | | |
| Type | ID | Description |
| Symptoms | 100003 | Dyspnea |
| Symptoms | 100015 | Fatigue |
| . . . | | |
| History | 200010 | Congestive Heart Failure |
| . . . | | |
| Examination | 300024 | Jugular Venous Distension |
| Examination | 300011 | Rales |
| Examination | 300008 | Peripheral Edema |
| . . . | | |
| Tests | 400075 | EKG |
| Tests | 400262 | CBC |
| Tests | 400321 | Troponin |
| Tests | 400400 | CPK - MB |
| Tests | 400488 | Renal Function Panel |
| Tests | 400511 | CXR |
| . . . | | |
| Diagnoses | 500400 | Congestive Heart Failure |
| . . . | | |
| Therapy | 600001 | Admission to Emergency Department |
| Therapy | 600011 | Medication Reconciliation |
| Therapy | 600026 | Medication Compliance |
| Therapy | 600142 | Diuretics |
| Therapy | 600199 | Blood Pressure Control |
| | | |
| Branch | | |
| History | 200010 | Congestive Heart Failure admission within last 30 days |
| If yes | | |
| Therapy | 600011 | Medication Reconciliation |
| Therapy | 600026 | Medication Compliance |
| Therapy | 600143 | Modify Does of Diuretics |

442 — Medical Findings section
444 — Branch
446 — If yes section

FIG. 8

INTELLIGENT PROMPTING OF PROTOCOLS

CROSS REFERENCE TO RELATED APPLICATIONS

The present application is a continuation application of U.S. patent application Ser. No. 16/774,236 entitled INTELLIGENT PROMPTING OF PROTOCOLS, filed Jan. 28, 2020 which is a continuation of U.S. patent application Ser. No. 14/629,215 entitled INTELLIGENT PROMPTING OF PROTOCOLS, filed Feb. 23, 2015, which issued as U.S. Pat. No. 10,600,505, which claims priority to U.S. provisional patent application No. 61/943,252, filed Feb. 21, 2014, the entire disclosures of which are expressly incorporated herein by reference.

BACKGROUND

Healthcare providers are increasingly using electronic medical records for the management of patient health data. The records typically include patient notes, where a detailed account of a caregiver's encounter with the patient is recorded. For example, the patient note may include a record of the patient's chief complaint, the symptoms that the patient was exhibiting, the results of an examination, the patient's relevant medical history, the results of any tests that were performed, the diagnosis, and the therapy.

Healthcare providers may want to or be required to document certain medical findings during patient encounters depending on the reason for the patient encounter. This has led to the development of various protocols for documenting patient encounters. Some medical records systems include many protocols and it may be difficult to identify appropriate protocols for use during a particular patient encounter.

SUMMARY

In general terms, this disclosure is directed to electronic medical records, and more particularly, to a caregiver interface for electronic medical records. In one possible configuration and by non-limiting example, the caregiver interface includes intelligent prompting of protocols. Various aspects are described in this disclosure, which include, but are not limited to, the following aspects.

In one aspect, a method of generating a user interface for use in documenting a patient encounter comprises: automatically identifying, with a computing device, at least one documentation protocol based on at least one element of the patient's medical record; and generating a user interface including at least one of the identified documentation protocols, the at least one identified documentation protocol identifying at least one medical finding.

In another aspect, a method generates a user interface for use in documenting a patient encounter. The method comprises receiving medical finding data through a user interface, the medical finding data identifying two or more medical findings; searching a database of documentation protocols, each documentation protocol in the database being linked in the database with at least one medical finding; identifying each documentation protocol in the database linked with at least one of the two or more medical findings; assigning a score to each documentation protocol identified in the act of identifying documentation protocols, each score assigned to a documentation protocol identified in the act of identifying documentation protocols being equal to the number of medical findings identified by the medical finding data entered through the user interface that are linked to the documentation protocol in the database; and displaying a user interface, the user interface comprising the identified documentation protocol having a score equal to or greater than a predetermined threshold score.

In another aspect, a method generates a user interface for use in documenting a patient encounter. The method comprises receiving medical finding data through a user interface, the medical finding data identifying two or more medical findings; searching a database of documentation protocols, each documentation protocol in the database being linked in the database with at least one medical finding; identifying each documentation protocol in the database linked with at least one of the two or more medical findings; upon identifying two or more documentation protocols, merging the identified documentation protocols; filtering duplicate medical findings from the merged documentation protocols; and displaying a user interface, the user interface comprising the merged identified documentation protocol.

A system comprising a data store encoded on a memory device. The data store comprises a database identifying a plurality of documentation protocols and linking at least one of the documentation protocols to one or more medical findings. The system further comprises an input apparatus and a computing device in data communication with the data store and the input apparatus. The computing device is programmed to receive medical finding data input through the input apparatus, the medical finding data identifying a medical finding, search the database of documentation protocols, identify a documentation protocol linked to the medical finding, and generate a user interface, the user interface comprising the identified documentation protocol linked to the medical finding.

This summary is provided to introduce a selection of concepts in a simplified form that are further described below in the detailed description. This summary is not intended to identify key features or essential features of the claimed subject matter, nor is it intended that this summary be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIG. 5 is an example of a congestive heart failure protocol.

FIG. 6 is an example of a bacterial pneumonia protocol.

FIG. 7 is an example of a merged protocol formed by merging the congestive heart failure protocol illustrated in FIG. 5 and the bacterial pneumonia protocol of FIG. 6.

FIG. 8 is an example of a branching protocol.

DETAILED DESCRIPTION

Figure 1:
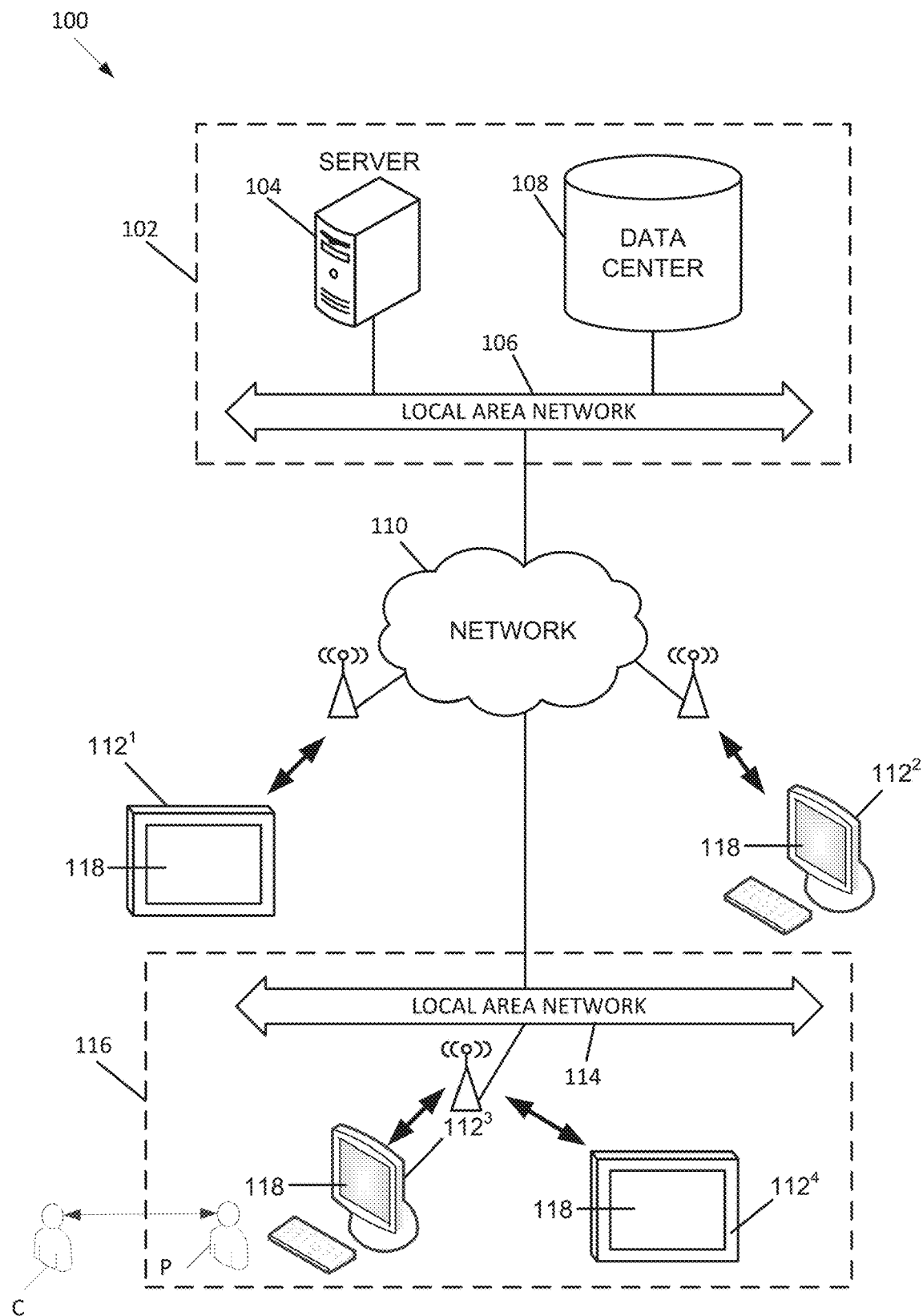
FIG. 1 is a schematic diagram illustrating an exemplary electronic medical records system.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Whenever appropriate, terms used in the singular also will include the plural and vice versa. The use of "a" herein means "one or more" unless stated otherwise or where the use of "one or more" is clearly inappropriate. The use of "or" means "and/or" unless stated otherwise. The use of "comprise," "comprises," "comprising," "include," "includes," and "including" are interchangeable and not intended to be limiting. The terms "such as," "for example," and "e.g." also are not intended to be limiting. For example, the term "including" shall mean "including, but not limited to." Furthermore, where the description of one or more embodiments uses the term "comprising," those skilled in the art would understand that, in some specific instances, the embodiment or embodiments can be alternatively described using the language "consisting essentially of" and/or "consisting of."

Additionally, language such as "examples," "some examples," "possible examples," "exemplary," "some exemplary," "embodiments," "some embodiments," and "alternative embodiments" also is not intended to limit the various possible embodiments covered by the attached claims in any way. Thus, for example, language such as "embodiments" and "some embodiments" denotes a single embodiment, some of the possible embodiments, or all of the possible embodiments.

In general, the present disclosure describes systems and methods involving the selection of appropriate protocols for documenting care given to a patient. Example protocols may take many and varied forms. In some examples, the protocols are documentation protocols, which are used as guidelines for documenting a patient encounter. Example documentation protocols identify specific medical findings that a caregiver may determine during a patient encounter. In some embodiments, a documentation protocol is used to ensure that similar patients are examined uniformly, to document information required for reimbursement or regulatory compliance, or to elicit information for use in a research study. Other protocols are medical protocols or procedures for assessing, evaluating, diagnosing, or treating a medical condition—whether the medical condition is a physical or mental condition—and the like. In some embodiments, the protocols are developed by the caregiver, a supervisor, a health care facility administrator, a health insurance provider, a research organization, or a government entity.

In some embodiments, the protocols are configured to be used by caregivers, such as physicians, nurses, physician's assistants, psychologists, counselors, therapists, opticians, optometrists, dentists, medical assistants, secretaries, receptionists, emergency medical technicians or other first responders, and other people that are involved with providing care to a patient and/or documenting clinical visits with a patient.

Because there are often many protocols available to a caregiver, identifying and selecting an appropriate protocol or protocols for use during a particular patient encounter can be challenging. In some embodiments, the protocols are selected based on one or more of the primary purpose for the patient encounter, medical findings identified during the patient encounter, and medical findings in historical medical records.

Additionally, multiple protocols may be selected as appropriate for a particular patient encounter. In some embodiments, to avoid duplicating findings that are included in multiple protocols, the protocols are merged to form a single patient encounter protocol. In some embodiments, the patient encounter protocol is formed from merging the individual protocols and filtering out duplicated findings. Additionally, in some embodiments, the findings are reordered so that related or similar findings are presented together. In some embodiments, the patient encounter protocol is formatted based on a template associated with the most appropriate protocol for the patient encounter.

In some embodiments, the system identifies appropriate protocols based on a single known diagnosis. In other embodiments, the system identifies appropriate protocols based on a list of possible diagnoses. The list of possible diagnoses is determined based on an initial finding, such as the chief complaint, or some initial findings that have been recorded during the patient encounter. Then, the protocols that are related to or share findings with the possible diagnoses are identified as being appropriate for use to document the patient encounter. In some embodiments, a list of protocols is presented to the caregiver. In other embodiments, one or more of the protocols may be automatically selected and incorporated into the user interface.

FIG. 1 illustrates an exemplary embodiment of an electronic healthcare system 100. Caregivers interact with the electronic healthcare system 100 to document patient encounters and/or access medical information via various user-friendly interfaces. The system 100 includes a medical information records system 102, a network 110, and user computing devices 112. User computing devices 112 include stand-alone computing devices $112^1$ and $112^2$ as well as networked computing devices $112^3$ and $112^4$ that are connected to local area network 114.

In general, a caregiver C utilizes the system 100 to document patient encounters, such as with a patient P, and to investigate the causes and/or resulting medical problems related to the patient P's condition. For example, the caregiver C can utilize a caregiver interface 118 to search for various medical diagnoses and/or findings associated with the patient P. Diagnoses and findings are examples of medical items. In some embodiments, medical findings include symptoms that the patient P is experiencing, relevant medical history or family medical history of the patient P, findings from a physical or mental examination of the patient P, tests performed on the patient P and the results of those tests, and therapies performed or prescribed.

Some embodiments of medical information records system 102 include a server 104 and a data center 108 that communicate across local area network 106. The medical information records system 102 operates to store medical information, including medical records of patients, diagnoses, findings, and protocols, and to send selected portions of the medical information across the network 110 when requested by a computing device 112. The medical information records system 102 can be located at the same location (such as in the same room, building, or facility) as one or more of the computing devices 112. Alternatively, the medical information records system 102 is located remote from the computing devices 112, such as in a different building, city, state, country, or continent.

In some embodiments, other electronic medical records systems transfer data to the medical information records system 102. In at least one alternate embodiment, the other electronic medical records may utilize alternate medical terminology that is different than medical terminology used in the medical information records system 102, and thus translation of the information is necessary for the medical information records system 102 to appropriately use the information. In some embodiments, the medical information records system 102 includes a mapping structure that receives medical information (e.g., diagnoses and/or medical findings) from the other medical records systems and converts them into a terminology utilized by the medical information records system 102.

The server 104 controls access to information stored in the medical information records system 102, in some embodiments. In at least one example embodiment, the server 104 is a computing device 112 that includes a database software application, such as the SQL SERVER® database software distributed by MICROSOFT® Corporation. In some other possible embodiments, the server 104 is a Web server or a file server. When a request for medical information is received by the server 104, the server 104 retrieves the medical information from the data center 108 and sends it across the network 110 to the computing device 112 that requested it.

The data center 108 is a data storage device configured to store a variety of medical information. Examples of the data center 108 include a hard disk drive, a collection of hard disk drives, digital memory (such as random access memory), a redundant array of independent disks (RAID), or other data storage devices. In some embodiments, medical information is distributed across multiple local or remote data storage devices. The data center 108 stores data in an organized manner, such as in a hierarchical or relational database structure, or in lists and other data structures such as tables. Although the data center 108 is illustrated as being separated from the server 104, in some embodiments the data center 108 is located on the server 104.

The network 110 communicates digital data between one or more computing devices, such as between the medical information records system 102 and the computing devices 112. Examples of the network 110 include a local area network and a wide area network, such as the Internet.

In some embodiments, the network 110 includes a wireless communication system, a wired communication system, or a combination of wireless and wired communication systems. A wired communication system can transmit data using electrical or optical signals in various possible embodiments. Wireless communication systems typically transmit signals via electromagnetic waves, such as in the form of optical signals or radio frequency (RF) signals. A wireless communication system typically includes an optical or RF transmitter for transmitting optical or radio frequency signals, and an optical or RF receiver for receiving optical or radio frequency signals. Examples of wireless communication systems include Wi-Fi communication devices (such as utilizing wireless routers or wireless access points), cellular communication devices (such as utilizing one or more cellular base stations), and other wireless communication devices.

Although the medical information records system 102 is illustrated as being separated from the computing devices 112 by the network 110, the medical information records system 102 is alternatively a local data storage device of at least one of the computing devices 112 or is connected to the same local area network 114 as the computing devices 112.

In some example embodiments, the computing devices 112 are computing devices used by the caregiver C that display the caregiver interface 118.

In some embodiments, some of the computing devices 112 are located at a point of care, such as within a room where a caregiver C and a patient P interact. In other embodiments, some of the computing devices 112 are located near the point of care, such as in a hallway or nearby room. However, in other possible embodiments, some of the computing devices 112 are not located near the point of care and can be in separate buildings, facilities, or even remote geographic locations.

In some embodiments, the computing devices 112 are mobile computing devices, such as tablet computers (such as the iPad® device available from Apple, Inc., or other tablet computers running an operating system like the Microsoft Windows operating system from Microsoft Corporation of Redmond, Washington, or the Android operating system from Google Inc. of Mountain View, California), smartphones, or other mobile computing devices. In some embodiments, computing devices 112 include a touch sensitive display for receiving input from a user either by touching with a finger or using a stylus. In some of these embodiments, the caregiver C carries a computing device 112 to the point of care for documenting an encounter with the patient P. Example technologies and devices for control and inputting data to medical information systems are disclosed in U.S. patent application Ser. No. 13/401,571, entitled TOUCH INTERFACE FOR DOCUMENTATION OF PATIENT ENCOUNTER and filed on Feb. 21, 2012, the entire disclosure of which is incorporated by reference herein.

In example embodiments, the electronic healthcare system 100 includes stand-alone computing devices 112$^1$ and 112$^2$, as well as networked computing devices 112$^3$ and 112$^4$. Stand-alone computing devices 112$^1$ and 112$^2$ connect directly to network 110 and are not part of an additional local area network. In some embodiments, the stand-alone computing devices 112$^1$ and 112$^2$ connect through a wireless network, such as a cellular telephone network. Networked computing devices 112$^3$ and 112$^4$ are connected to a local area network 114 which may be within a facility 116, such as a hospital, clinic, office, or other building. In some embodiments, a connection to the local area network 114 is made wirelessly through a wireless access point connected to the local area network 114. In this example, stand-alone computing device 112$^1$ and networked computing device 112$^4$ are mobile computing devices, while stand-alone computing device 112$^2$ and networked computing device 112$^3$ are desktop computer computing devices. More or fewer computing devices 112 are included in other possible embodiments and can be located in one or more different facilities, buildings, or geographic locations.

Figure 2:
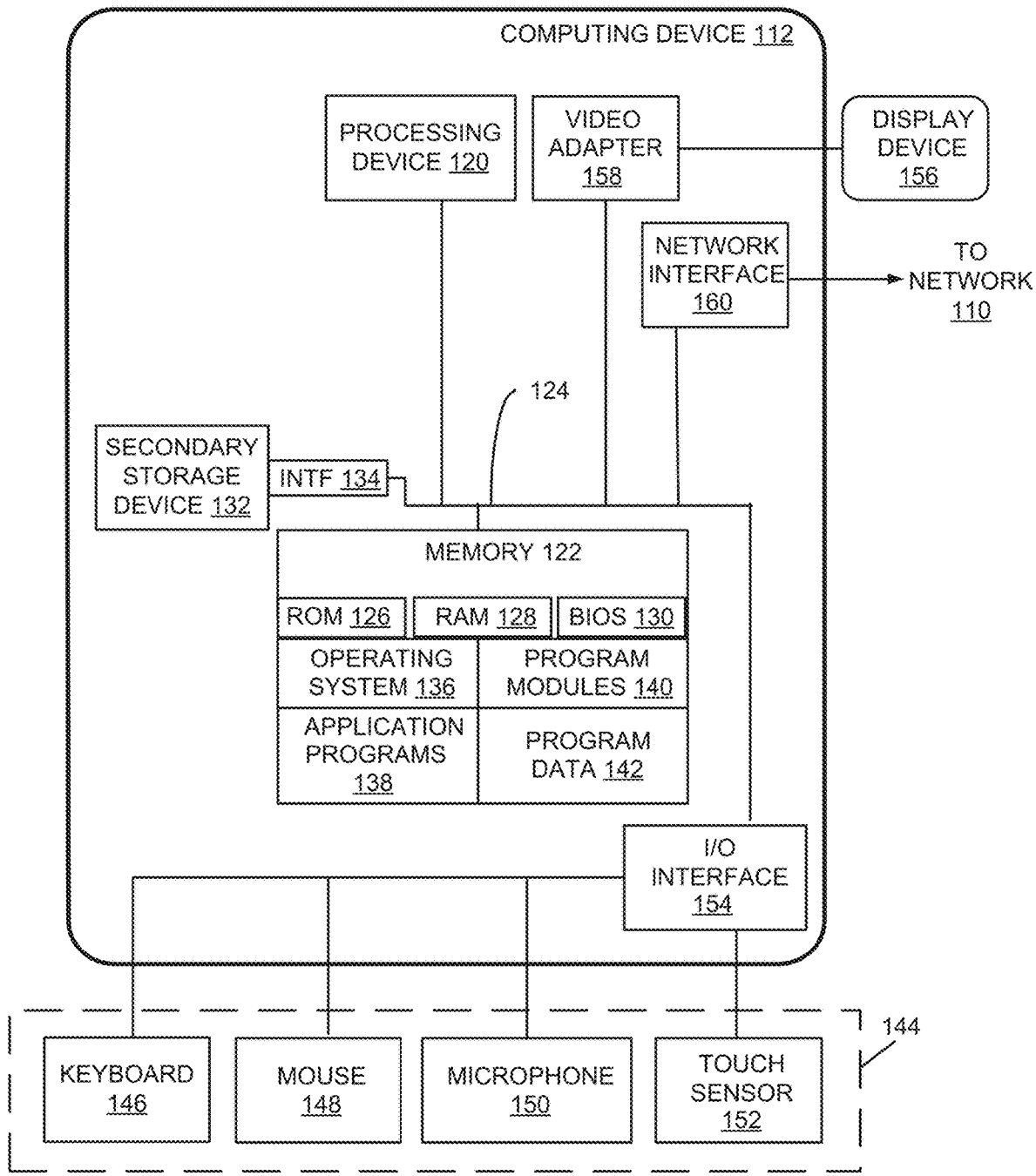
FIG. 2 is a schematic block diagram illustrating computer architecture for a computing device implemented in the electronic medical records system of FIG. 1.

FIG. 2 illustrates an exemplary architecture of a computing device that can be used to implement aspects of the present disclosure, including the server 104 or the computing devices 112, and will be referred to herein as the computing device 112. One or more computing devices 112, such as the type illustrated in FIG. 2, are used to execute the operating system, application programs, and software modules (including the software engines) described herein.

The computing device 112 includes, in some embodiments, at least one processing device 120, such as a central processing unit (CPU). A variety of processing devices are available from a variety of manufacturers, for example, Intel or Advanced Micro Devices. In this example, the computing device 112 also includes a system memory 122, and a system bus 124 that couples various system components including the system memory 122 to the processing device 120. The system bus 124 is one of any number of types of bus structures including a memory bus or memory controller, a peripheral bus, and a local bus using any of a variety of bus architectures.

Examples of computing devices suitable for the computing device 112 include a desktop computer, a laptop computer, a tablet computer, a mobile phone device such as a smart phone, or other devices configured to process digital instructions.

The system memory 122 includes read only memory 126 and random access memory 128. A basic input/output system 130 containing the basic routines that act to transfer information within computing device 112, such as during start up, is typically stored in the read only memory 126.

The computing device 112 also includes a secondary storage device 132 in some embodiments, such as a hard disk drive, for storing digital data. The secondary storage device 132 is connected to the system bus 124 by a secondary storage interface 134. The secondary storage devices 132 and their associated computer readable media provide nonvolatile storage of computer readable instructions (including application programs and program modules), data structures, and other data for the computing device 112.

Although the exemplary environment described herein employs a hard disk drive as a secondary storage device 132, other types of computer readable storage media are used in other embodiments. Examples of these other types of computer readable storage media include magnetic cassettes, flash memory or other solid state memory technology, digital video disks, Bernoulli cartridges, compact disc read only memories, digital versatile disk read only memories, random access memories, or read only memories. Some embodiments include non-transitory media.

A number of program modules can be stored in secondary storage device 132 or memory 122, including an operating system 136, one or more application programs 138, other program modules 140, and program data 142. The data center 108 may be stored at any location in the memory 122, such as the program data 142, or at the secondary storage device 132.

In some embodiments, computing device 112 includes input devices 144 to enable the caregiver C to provide inputs to the computing device 112. Examples of input devices 144 include a keyboard 146, pointer input device 148, microphone 150, and touch sensor 152. A touch-sensitive display device is an example of a touch sensor 152. Other embodiments include other input devices 144. The input devices 144 are often connected to the processing device 120 through an input/output interface 154 that is coupled to the system bus 124. These input devices 144 can be connected by any number of input/output interfaces, such as a parallel port, serial port, game port, or a universal serial bus. Wireless communication between input devices 144 and interface 154 is possible as well, and includes infrared, BLUETOOTH® wireless technology, 802.11a/b/g/n, cellular, or other radio frequency communication systems in some possible embodiments.

In this example embodiment, a touch sensitive display device 156 is also connected to the system bus 124 via an interface 154, such as a video adapter 158. In some embodiments, the display device 156 is a touch sensitive display device. A touch sensitive display device 156 includes a sensor for receiving input from a user when the user touches the display or, in some embodiments, gets close to touching the display. Such sensors can be capacitive sensors, pressure sensors, optical sensors, or other touch sensors. The sensors not only detect contact with the display, but also the location of the contact and movement of the contact over time. For example, a user can move a finger or stylus across the screen or near the screen to provide written inputs. The written inputs are evaluated and, in some embodiments, converted into text inputs.

In addition to the display device 156, the computing device 112 can include various other peripheral devices (not shown), such as speakers or a printer.

When used in a local area networking environment or a wide area networking environment (such as the Internet), the computing device 112 is typically connected to the network 110, 114 through a network interface, such as a wireless network interface 160. Other possible embodiments use other communication devices. For example, some embodiments of the computing device 112 include an Ethernet network interface, or a modem for communicating across the network 110, 114.

The computing device 112 typically includes at least some form of computer-readable media. Computer readable media includes any available media that can be accessed by the computing device 112. By way of example, computer-readable media include computer readable storage media and computer readable communication media.

Computer readable storage media includes volatile and nonvolatile, removable and non-removable media implemented in any device configured to store information such as computer readable instructions, data structures, program modules, or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 112.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

Figure 3:
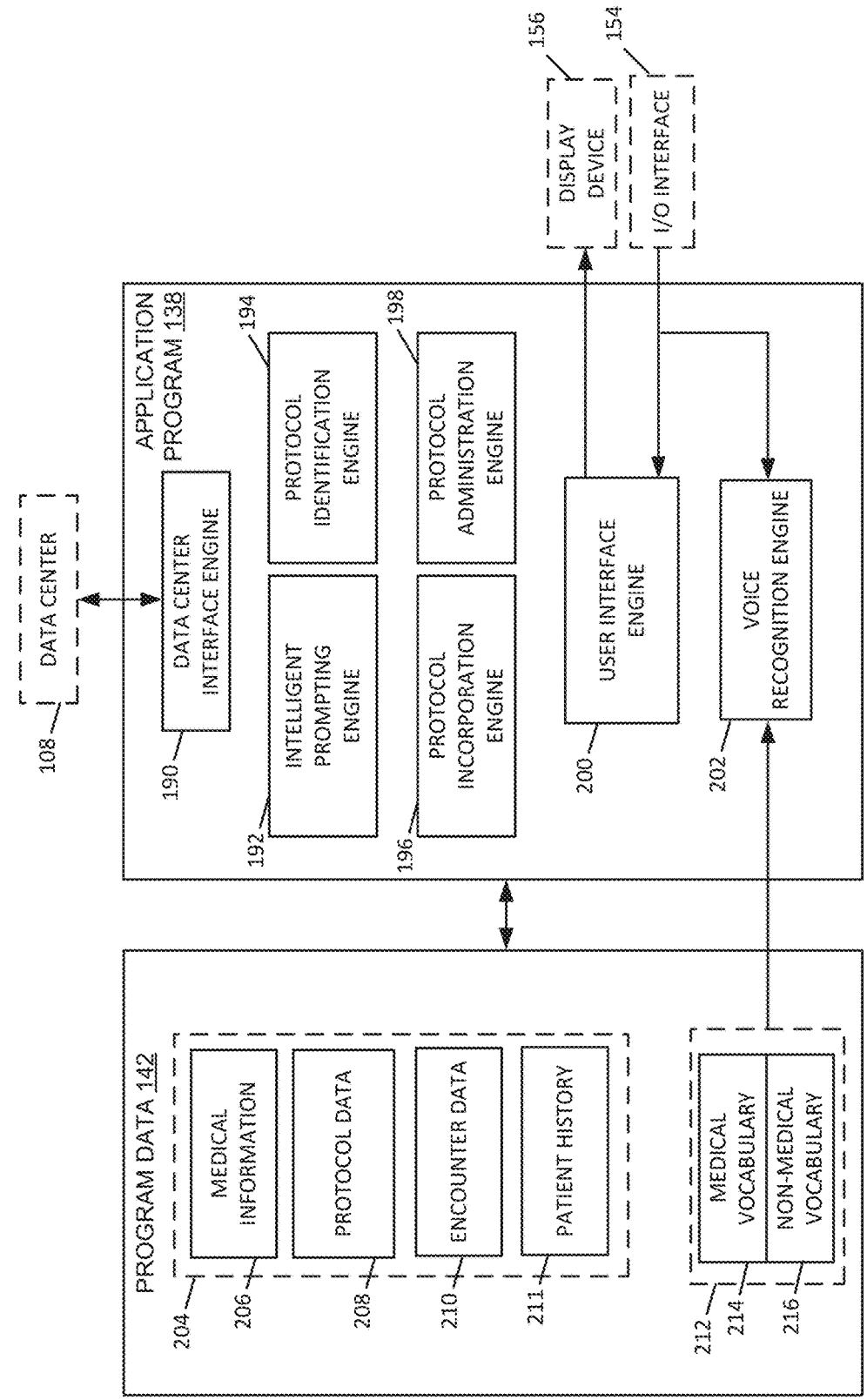
FIG. 3 is a schematic block diagram illustrating the architecture of an application program and program data for the electronic medical records system illustrated in FIG. 1.

FIG. 3 illustrates an exemplary architecture of the application program 138 and the program data 142 of the computing device 112 (shown in FIG. 2). The application program 138 includes a plurality of modules that, when executed by the processor, perform one or more operations of the application program 138. The modules include a data center interface engine 190, an intelligent prompting engine 192, a protocol identification engine 194, a protocol incorporation engine 196, a protocol administration engine 198, a user interface engine 200, and a voice recognition engine 202.

Program data 142 is stored in a data storage device, such as the memory 122 or the secondary storage device 132 (shown in FIG. 2). In some embodiments, program data 142 includes user interface data 204 and a word base 212. The user interface data 204 includes the user interfaces or data used to generate user interfaces or information that is displayed on the user interfaces. Examples of the user interface data 204 include medical information 206, protocol data 208, encounter data 210, and patient history 211. The word base 212 includes, for example, medical vocabulary 214 and non-medical vocabulary 216.

In an exemplary embodiment, the data stored in program data 142 can be represented in one or more files having any format usable by a computer. Examples include text files formatted according to a markup language and having data items and tags to instruct computer programs and processes how to use and present the data item. Examples of such formats include html, xml, and xhtml, although other formats for text files can be used. Additionally, the data can be represented using formats other than those conforming to a markup language.

In some embodiments, the application program 138 communicates with the data center 108 of the healthcare information management system 102, and also communicates with the display device 156 and the input/output interface 154 of the computing device 112. Such communication between the application program 138 and healthcare information management system 102 can occur through the server 104. In some possible embodiments, the application program 138 resides on the computing device 112, while in other possible embodiments, the application program 138 resides on a server. For example, if the application program 138 resides on the server 104, the caregiver interface 118 can be presented as a web page file that is communicated to the computing device 112. In this example, the computing device 112 receives the web page file from the server 104 and generates the caregiver interface 118 using a Web browser software application.

The data center interface engine 190 operates to download data from the data center 108. The data center interface engine 190 can be configured to download data representing medical information 206, protocol data 208, and patient history 211 from the data center 108. In some embodiments, the data center interface engine 190 is configured to interface with more than one data center 108.

The intelligent prompting engine 192 operates to present a list of medical findings to a caregiver C for use in documenting a patient encounter. Details on how the system 102 intelligently prompts the caregiver C based on information stored in the data center 108 and how the intelligent prompting engine 192 functions are discussed in detail in U.S. Pat. No. 5,823,949, entitled INTELLIGENT PROMPTING and issued on Oct. 20, 1998, the entire disclosure of which is incorporated by reference herein.

The protocol identification engine 194 operates to identify and present a list of relevant protocols to a caregiver C for use in documenting a patient encounter. The protocol incorporation engine 196 operates to incorporate one or more protocols into the note workspace of a patient record. The protocol administration engine 198 operates to provide an administrative interface for creating or editing protocols.

The user interface engine 200 operates to generate and present a user interface, such as a graphical user interface, to a caregiver C. In some embodiments, the user interface engine 200 transmits the user interface to display device 156 over the video adapter 158 (shown in FIG. 2).

The user interface engine 200 also receives inputs from a caregiver C. In some embodiments, the inputs are received through the input/output interface 154. Examples of such inputs include inputs from a keyboard 146, a pointer input device 148, a microphone 150, or a touch sensor 152 (all shown in FIG. 2). In some embodiments, the display device 156 is touch sensitive, and touch inputs are received from a caregiver C through the display device 156. Examples of inputs from a caregiver C include descriptions and/or names of medical findings and/or answers to questions presented through the input/output interface 154 by the intelligent prompting engine 192.

The voice recognition engine 202 processes voice inputs provided by a caregiver C. In this example, voice recognition engine 202 receives voice inputs from input/output interface 154. Voice recognition engine 202 utilizes a word base 212, which includes medical vocabulary 214 and non-medical vocabulary 216, to identify the words input by the caregiver C. In example embodiments, the voice recognition engine 202 can be implemented with any suitable voice recognition software applications. An example of a voice recognition engine 202 is the NUANCE® Speech-Magic™ software application. In some embodiments, the voice recognition engine 202 operates to compare an input waveform to a set of word waveforms and to identify the word or words that have the closest match.

In some embodiments, the output of the voice recognition engine 202 is either a command or a data entry. Commands are passed to the user interface engine 200 and cause the application program 138 to take an action. The data entry is stored in the current record 176 of program data 142.

The medical information 206 includes information such as medical findings and diagnoses, as well as the relationships between them. In some embodiments, the medical information 206 includes other information as well. The medical information 206 is used by the various modules of the application program 138. In some embodiments, the medical information 206 is retrieved from the data center 108 by the data center interface engine 190.

The protocol data 208 includes information about protocols that are defined in the electronic healthcare system 100. In some embodiments, the protocol data 208 is retrieved from the data center 108 by the data center interface engine 190.

The encounter data 210 includes information recorded during the current patient encounter. In some embodiments, the encounter data 210 includes other information as well. In some embodiments, after the encounter data 210 has been completed, the data center interface engine 190 transmits the encounter data 210 to the data center 108. In some embodiments, the encounter data 210 becomes a historical data record that can be used in subsequent interactions.

Figure 4:
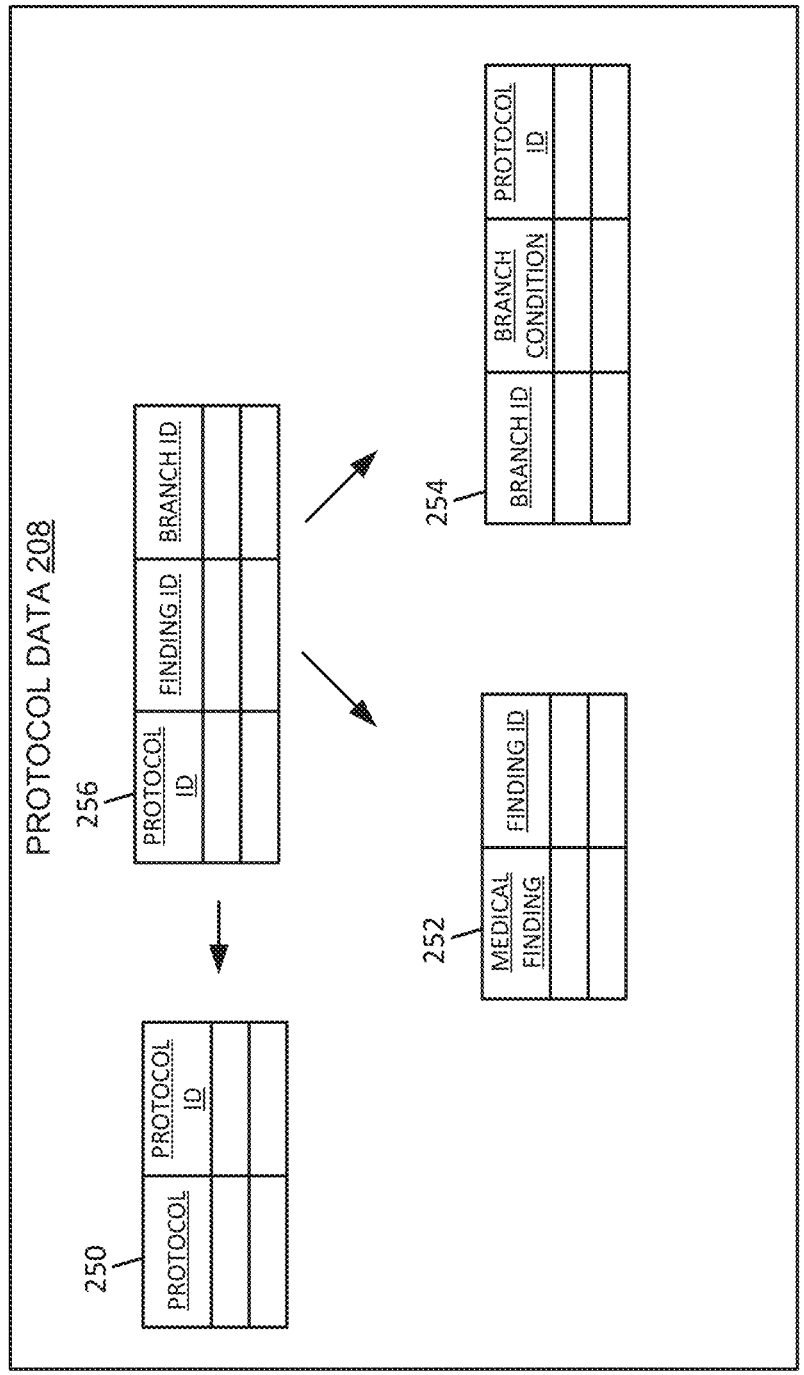
FIG. 4 is an example format of the protocol data illustrated in FIG. 3.

FIG. 4 illustrates an example format of the protocol data 208. In this example, the protocol data 208 is contained in a plurality of data structures in the form of tables utilizing data IDs. Data ID fields are used to map data between tables and user interfaces. Other embodiments include other types of data structures and other methods of linking data structures.

In an example embodiment, the protocol data 208 includes a protocol table 250, a medical findings table 252, a branch table 254, and a protocol-finding relationship table 256. Additional tables are included in other embodiments as needed. Further, some embodiments include different table structures, such as to merge data from multiple tables into a single table or to separate data from a single table into multiple tables. Various embodiments can include any suitable structure of tables or other mechanism to link or otherwise relate data, such as relating select medical findings to select protocols.

The protocol table 250 includes a list of available protocols and maps each protocol to a unique protocol ID. The protocols identify groups of medical findings that a caregiver C may wish to document in certain circumstances. In some embodiments, the protocols are described by a name or short phrase that may be easy for a caregiver C to recognize. The unique protocol ID can be used to refer to the protocol in other data structures.

The medical findings table 252 includes a list of the available medical findings, and maps each medical finding to a unique finding ID. Medical findings identify a physical or mental characteristic of a person, such as the patient P or a relative of the patient P. In some embodiments, medical findings include symptoms that a patient P is experiencing, relevant medical history of the patient P or the patient's family, findings from a physical or mental examination of the patient P, diagnoses of the patient P, tests performed on a patient P and the results of the tests, and therapy performed or prescribed. Each finding has a unique finding ID, which can be used to refer to the medical finding in other data structures. Some embodiments, for example, include a medical findings table 252 having more than 200,000 possible medical findings.

In some embodiments, the medical findings are organized in a hierarchical structure that provides various levels of detail for medical findings. For example, a hierarchical structure can include multiple levels, where findings in the first level are generic descriptions of medical findings, and findings in the lower levels include more detailed descriptions of those medical findings. For example, a first level medical finding might be a cough, while a second level medical finding associated with the cough might be a brassy cough. Additional data structures are provided in some embodiments to link medical findings to the various levels in a hierarchical structure. In these embodiments, the higher level medical finding is sometimes referred to as a parent finding, while the lower lever finding is sometimes referred to as a child finding. The terms parent finding and child finding are relative and, accordingly, in some embodiments, a particular finding may be both a child of a higher level finding and a parent of a lower level finding. Some embodiments further associate each finding with a category, such as by including a category column (not shown) in the medical findings table 252. Examples of findings categories include a symptom, a medical history, an examination finding, a diagnosis, a test, a therapy, and a designation of the medical finding as being a physical or mental finding. Other embodiments include more or fewer categories.

The branch table 254 includes a list of branches, which include branch conditions and refer to protocols. The branch table 254 maps each branch to a unique branch ID, which may be referred to by other data structures. The branch condition is a condition that when true indicates that branching should occur. In some embodiments, the branch condition is a Boolean value, such as TRUE or FALSE, indicating that the branch should occur if the finding is present or absent, respectively. In other embodiments, the branch condition is a comparison to a threshold value, such as body temperature or blood glucose level above a certain value. Other embodiments of the branch condition are possible as well. The protocol ID contains the unique ID of a protocol in the protocol table 250. In some embodiments, when a branch condition is true, the protocol referred to by the protocol ID is incorporated into the note workspace.

The protocol-finding relationship table 256 associates each protocol with the relevant medical findings and also identifies branch conditions for the medical finding with respect to the protocol. In some embodiments, each protocol is associated with one or more medical findings. In some embodiments, the protocol-finding relationship table 256 includes a row for each medical finding associated with a protocol. The protocol ID contains the unique ID of a protocol in the protocol table 250. The medical finding ID includes the unique ID of a medical finding in the medical findings table 252. The branch ID contains the unique ID of a branch in the branch table 254. In some embodiments, the branch ID is set null to indicate that the protocol does not branch at the specified medical finding.

This example structure of the protocol data 208 illustrated in FIG. 4 is an example of a possible structure. Various other embodiments utilize other data structures and contain more or less data fields as desired.

Although the protocol data 208 is described as residing on the computing device 112, other possible embodiments store the protocol data 208 in other locations. For example, in some embodiments, the protocol data 208 is stored on the server 104 or in the data center 108, rather than in the computing device 112. Alternative embodiments provide the caregiver interface 118 through a Web browser software application, such as to provide the caregiver interface 118 as a service (e.g., Software as a Service). In this example, the server 104 performs many of the operations described herein instead of the computing device 112. Alternatively, in another possible embodiment, the computing device 112 stores the downloaded historical records 164 in another database, such as on another computing device.

FIG. 5 is a conceptual example of a congestive heart failure protocol 290 for documenting congestive heart failure during a patient encounter. In this example, the congestive heart failure protocol 290 includes a list 292 of medical findings. The list 292 is ordered by medical finding type or category and includes a description and an ID for each medical finding.

The congestive heart failure protocol 290 includes the symptoms Dyspnea (ID: 100003) and Fatigue (ID: 100015). This congestive heart failure protocol 290 prompts the caregiver C to document whether these symptoms are present.

This example congestive heart failure protocol 290 also includes the history finding of Congestive Heart Failure (ID: 200010). This congestive heart failure protocol 290 prompts the caregiver C to document whether the patient P has a history of congestive heart failure.

This example congestive heart failure protocol 290 also includes the examination findings of Jugular Venous Distension (ID: 300024), Rales (ID: 300011), and Peripheral Edema (ID: 300008). This congestive heart failure protocol 290 prompts the caregiver C to document whether these findings are present based on an examination of the patient P.

This example congestive heart failure protocol 290 also includes the test findings of EKG (ID: 400075), CBC (ID: 400262), Troponin (ID: 400321), CPK-MB (ID: 400400), Renal Function Panel (ID: 400488), and CXR (ID: 400511). This congestive heart failure protocol 290 prompts the caregiver C to document whether these tests have been performed in the past, have been ordered, and/or the results of the tests.

The congestive heart failure protocol 290 also includes the diagnosis of Congestive Heart Failure (ID: 500400). This congestive heart failure protocol 290 prompts the caregiver C to document a diagnosis of congestive heart failure as appropriate.

The congestive heart failure protocol 290 also includes the therapies Admission to Emergency Department (ID: 600001), Medication Reconciliation (ID: 600011), Medication Compliance (ID: 600026), Diuretics (ID: 600142), and Blood Pressure Control (ID: 600199). This congestive heart failure protocol 290 prompts the caregiver C to document whether these therapies were provided to the patient P.

In the congestive heart failure protocol 290, each of the medical findings in the list 292 includes a six digit numerical ID value. However, in other embodiments, other ID values are used. In some embodiments, the ID values are alphanumeric.

In this example, the creator of the congestive heart failure protocol 290 has determined that it is useful to document whether the findings identified in the list 292 are present during a patient encounter relating to congestive heart failure. For example, this protocol may be used when congestive heart failure has been diagnosed or is suspected. Other example protocols are directed towards other conditions or purposes and include other or different medical findings.

FIG. 6 is a conceptual example of a bacterial pneumonia protocol 340 for documenting bacterial pneumonia during a patient encounter. In this example, the bacterial pneumonia protocol 340 includes a list 342 of medical findings. The list 342 is ordered by medical finding type and includes a description and an ID for each medical finding.

The bacterial pneumonia protocol 340 includes the symptoms Dyspnea (ID: 100003), Productive Cough (ID: 100014), Shaking Chills (ID: 100050), and Confusion (ID: 100091). A caregiver utilizing this protocol is able to document whether these symptoms are present in the patient. This bacterial pneumonia protocol 340 prompts the caregiver C to document whether these symptoms are present in the patient P.

In contrast to the example congestive heart failure protocol 290, this example bacterial pneumonia protocol 340 does not include any history findings.

This example bacterial pneumonia protocol 340 includes the examination findings of Tachycardia (ID: 300063), Increased Respiratory Rate (ID: 300079), Confusion (ID: 300091), Blue Lips (ID: 300102), and Decreased Breath Sounds (ID: 300105). This bacterial pneumonia protocol 340 prompts the caregiver C to document whether these findings are present based on an examination of the patient P.

This example bacterial pneumonia protocol 340 also includes the test findings of Pulse Oximetry (ID: 400201), CXR (ID: 400511), and CBC (ID: 400262). This bacterial pneumonia protocol 340 prompts the caregiver C to document whether this test has been performed in the past, has been ordered, and/or the results of the test.

The bacterial pneumonia protocol 340 also includes the diagnosis of Bacterial pneumonia (ID: 500005). This bacterial pneumonia protocol 340 prompts the caregiver C to document a diagnosis of bacterial pneumonia as appropriate.

The bacterial pneumonia protocol 340 also includes the therapies Medication Reconciliation (ID: 600011), Oxygen (ID: 600045), and Antibiotics (ID: 600188). This bacterial pneumonia protocol 340 prompts the caregiver C to document whether these therapies were provided to the patient P.

In this example, the creator of the bacterial pneumonia protocol 340 has determined that it is useful to document whether these findings are present during a patient encounter relating to bacterial pneumonia. For example, this protocol may be used when bacterial pneumonia has been diagnosed or is suspected.

Alternative protocols for congestive heart failure and bacterial pneumonia can include different medical findings than those illustrated and described herein. Additionally, other embodiments can include protocols for medical conditions or purposes other than, or in addition to, congestive heart failure and bacterial pneumonia.

FIG. 7 is a conceptual example of a merged protocol 390. In this example, the merged protocol 390 is generated from the congestive heart failure protocol 290 and the bacterial pneumonia protocol 340. The congestive heart failure protocol 290 is directed towards documenting congestive heart failure during a patient encounter. The bacterial pneumonia protocol 340 is directed towards documenting bacterial pneumonia during a patient encounter. In this example, the merged protocol 390 includes a merged list 392 of medical findings. The merged list 392 is ordered by medical finding type and includes a description and an ID for each medical finding.

The merged list 392 includes all of the findings from list 292 of congestive heart failure protocol 290 and list 342 of bacterial pneumonia protocol 340. However, the findings that appear in both list 292 and list 342 (e.g., Dyspnea) are not duplicated. Each finding appears only once in merged list 392 of merged protocol 390. The findings from list 292 and list 342 are shown together and grouped by finding type. This ordering may be more intuitive to a caregiver C who has chosen to utilize the merged protocol 390. In other embodiments, the findings in the merged list 392 have other sequences or organizations.

FIG. 8 is a conceptual example of a branching protocol 440 used during a patient encounter for documenting congestive heart failure. The branching protocol 440 is similar to the congestive heart failure protocol 290 (shown in FIG. 5). In this example, the branching protocol 440 includes a list 442 of medical findings. In this example, the medical findings in list 442 are identical to the findings in list 292 of congestive heart failure protocol 290.

However, the branching protocol 440 additionally includes a branch 444 and the branch result findings list 446. The branch 444 is based on a history finding of Congestive Heart Failure Admission within the Last Thirty Days (ID: 200010). If a finding that matches the branch 444 is entered, then the findings in the branch result findings list 446 will also be provided to prompt the caregiver C to document the therapies of Medication Reconciliation (ID: 600011), Medication Compliance (ID: 600026), and Modify Dose of Diuretics (ID: 600143).

The example protocols of FIGS. 5-8 are included merely as illustrations and do not constitute medical advice. Similarly, in the system 100, the protocols are not intended to substitute for medical judgment, but are instead intended to facilitate an understanding of the apparatus and methods disclosed in this document and the documentation of patient encounters.

Figure 9A:
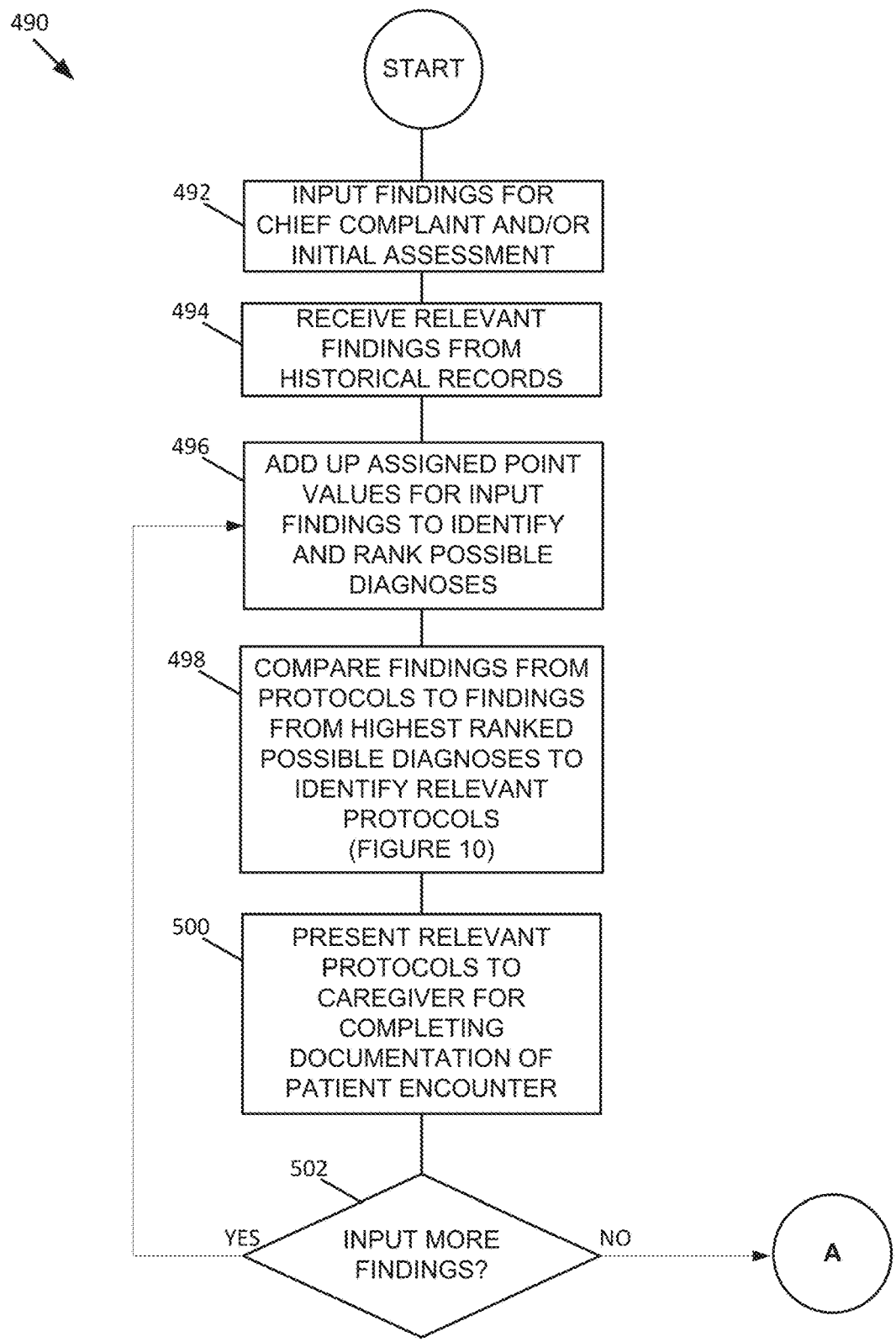
FIGS. 9A and 9B are flowcharts of a method for operating protocol identification and protocol incorporation engines illustrated in FIG. 2.
Figure 9B:
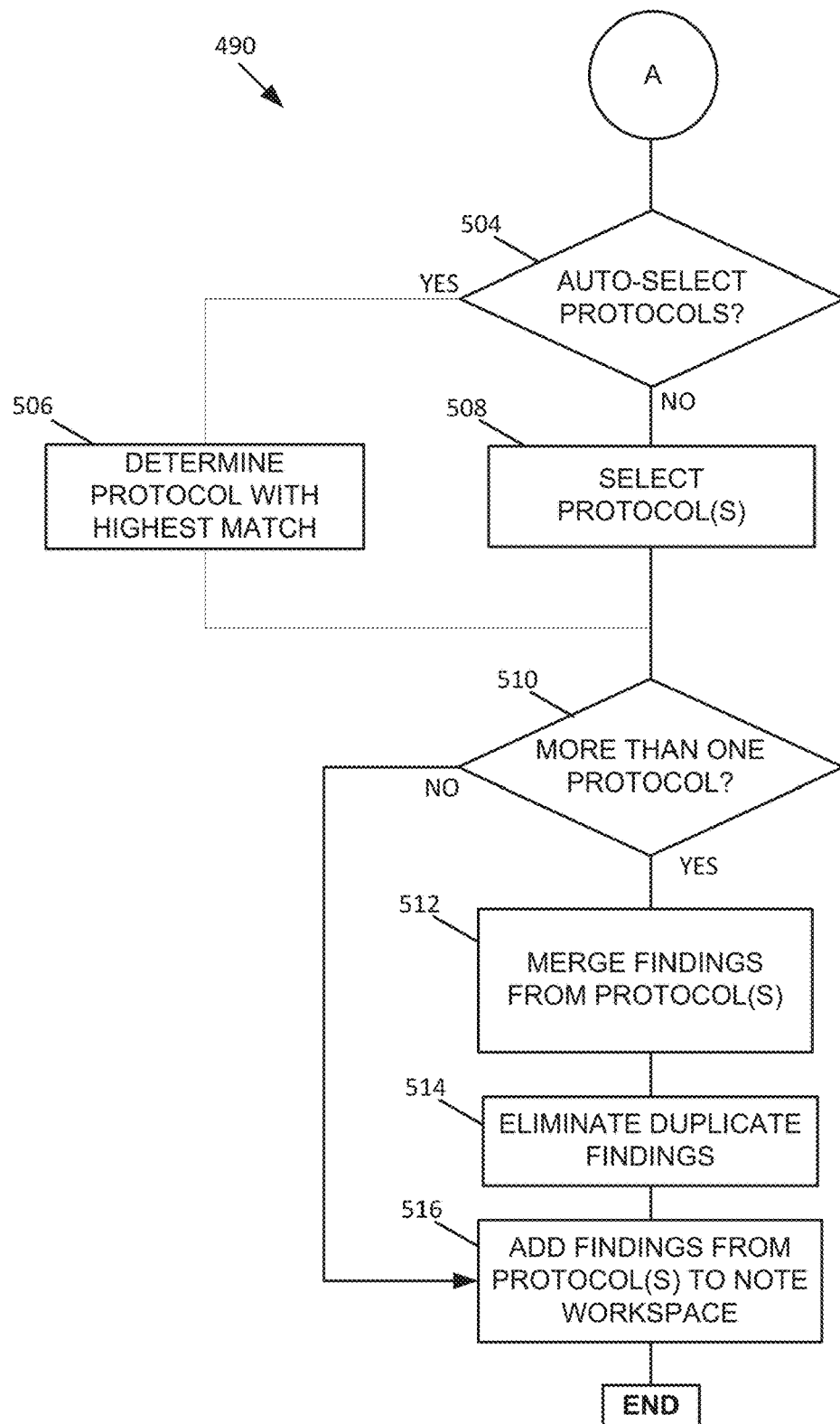

FIGS. 9A-B are flow charts illustrating an example method 490 of operating the protocol identification engine 194 and the protocol incorporation engine 196. In this example, the method 490 includes operations 492, 494, 496, 498, 500, 502, 504, 506, 508, 510, 512, 514, and 516. In some embodiments, the method 490 includes operations that are performed by a processor (such as the processing device 120, shown in FIG. 2). As used herein, methods include actions or operations that are performed by a user or executed by a computer, or combinations of these.

Initially, at operation 492, findings for chief complaint and/or initial assessment are input. The chief complaint is a medical finding. In some embodiments, the chief complaint is a medical finding of the type symptom. In some embodiments, the chief complaint is the reason for the patient encounter. However, some patient encounters do not have a chief complaint.

The initial assessment comprises one or more medical findings. In some embodiments, the initial assessment comprises findings related to a set of vital signs (e.g., body temperature, pulse rate, blood pressure, and respiratory rate). In other embodiments, the initial assessment includes other findings in addition to or instead of the vital signs. Additionally, in some embodiments, the initial assessment is not used.

In some embodiments, the chief complaint and/or initial assessment are input by the caregiver C through the I/O interface 154 (shown in FIG. 2), using, for example, the keyboard 146, the mouse 148, the microphone 150, or the touch sensor 152. In some embodiments, the chief complaint and/or initial assessment are received by the application program 138 through the user interface engine 200 or the voice recognition engine 202.

At operation 494, relevant findings from historical records are received. In some embodiments, the data center interface engine 190 retrieves findings from the data center 108 that are relevant or potentially relevant based on findings that have been input so far (e.g., the chief complaint, initial assessment, or other findings that have been input). In some embodiments, relevant findings are identified based on the intelligent prompting engine 192. For example, in some embodiments, the intelligent prompting engine 192 generates a list of medical findings that are related to possible diagnoses for the patient P based on the input findings. If historical records contain any of the findings in the list generated by the intelligent prompting engine 192, then those findings in the historical records are relevant in some embodiments. However, other embodiments are possible as well. Additionally, some embodiments do not perform this operation and historical records are not used. In these embodiments, operation 496 uses only the chief complaint and/or the initial assessment.

At operation 496, possible diagnoses are identified by adding up the point values associated with each input or relevant historical findings for each diagnoses. In some embodiments, the diagnoses are ranked based on total point value. In some of these embodiments, the five highest scoring diagnoses are identified. In other embodiments, all diagnoses with point values above a predetermined threshold are identified. In other embodiments, diagnoses with point values equal to or above a predetermined threshold are identified. As noted above, examples of this process are illustrated and described in more detail in U.S. Pat. No. 5,823,949, the entire disclosure of which has been incorporated by reference herein. In other embodiments, other methods of ranking and identifying diagnoses are used as well.

As described in more detail herein, at operation 498, the findings from the protocols are compared to the findings from the possible diagnoses that were ranked highest to identify relevant protocols.

At operation 500, the protocols identified in operation 498 are presented to a caregiver C for completing documentation of the patient encounter. In some embodiments, these protocols are presented automatically to the caregiver C. In other embodiments, these protocols are presented when the caregiver C requests the list of relevant protocols. Accordingly, in some embodiments, this operation 500 is not performed. Instead, the method 490 continues on to operation 502.

At operation 502, it is determined whether more findings will be input. In some embodiments, the caregiver C sends a command to the protocol identification engine 194 to indicate whether more findings will be input. Alternatively, in some embodiments, the caregiver C simply enters another finding, for example, through the intelligent prompting engine 192. In this embodiment for example, the system continuously identifies and presents protocols as the findings are entered. The user can continue this process until the desired protocols are displayed. In other embodiments, the protocol identification engine 194 determines that more findings are needed because not enough findings have been entered to match any protocols. Other embodiments are possible as well.

When another finding is input, the method 490 returns to operation 496. This part of the method 490 creates a loop through operations 496, 498, 500 and 502 for each finding that is input. Once it is determined in operation 502 that more findings will not be input, the method 490 continues to operation 504.

At operation 504, it is determined whether to auto-select a protocol. In some embodiments, the caregiver interface 118 prompts the caregiver C to choose whether a protocol should be auto-selected. In other embodiments, the caregiver C can choose to auto-select a protocol by clicking on a button on the caregiver interface 118. If the caregiver C chooses to auto-select a protocol, the method 490 continues to operation 506. If the caregiver C chooses not to auto-select a protocol, the method 490 continues to operation 508. Further, some embodiments do not include auto-select whatsoever.

At operation 506, the protocol with the highest match is determined and auto-selected. In some embodiments, the protocol with the highest match is the protocol with the highest score determined in operation 498. In other embodiments, other methods of identifying a protocol for auto-selection are used. For example, in some embodiments, the protocol is auto-selected based on the chief complaint. In some embodiments, only a single protocol is auto-selected. In other embodiments, multiple protocols are auto-selected.

Alternatively, at operation 508, the caregiver C selects one or more protocols using the caregiver interface 118. In some embodiments, the caregiver C highlights one or more protocols from a list of protocols and then clicks a button to merge the protocols. In other embodiments, the caregiver C double-clicks each of the protocols that are to be merged into a protocol for use with the current patient encounter.

An operation 510 is performed to determine whether more than one protocol was selected. If more than one protocol is selected, the method 490 performs the operation 512. Otherwise, the method 490 skips ahead to operation 516.

At operation 512, the findings from the plurality of selected protocols are merged. In some embodiments, this operation creates a merged list that contains an entry for each of the findings in the list of findings that are in each of the selected protocols. In some embodiments, the findings in the merged list are ordered by finding type. Additionally, branches in the selected protocols are preserved as well. In some embodiments, branches are compared and are merged when the branch conditions match.

At operation 514, duplicate findings are eliminated from the merged list of findings generated by operation 512. In some embodiments, duplicate findings are identified by the finding ID. If more than one finding in the merged list of findings have the same finding ID, then the duplicated findings are removed from the list.

Figure 12:
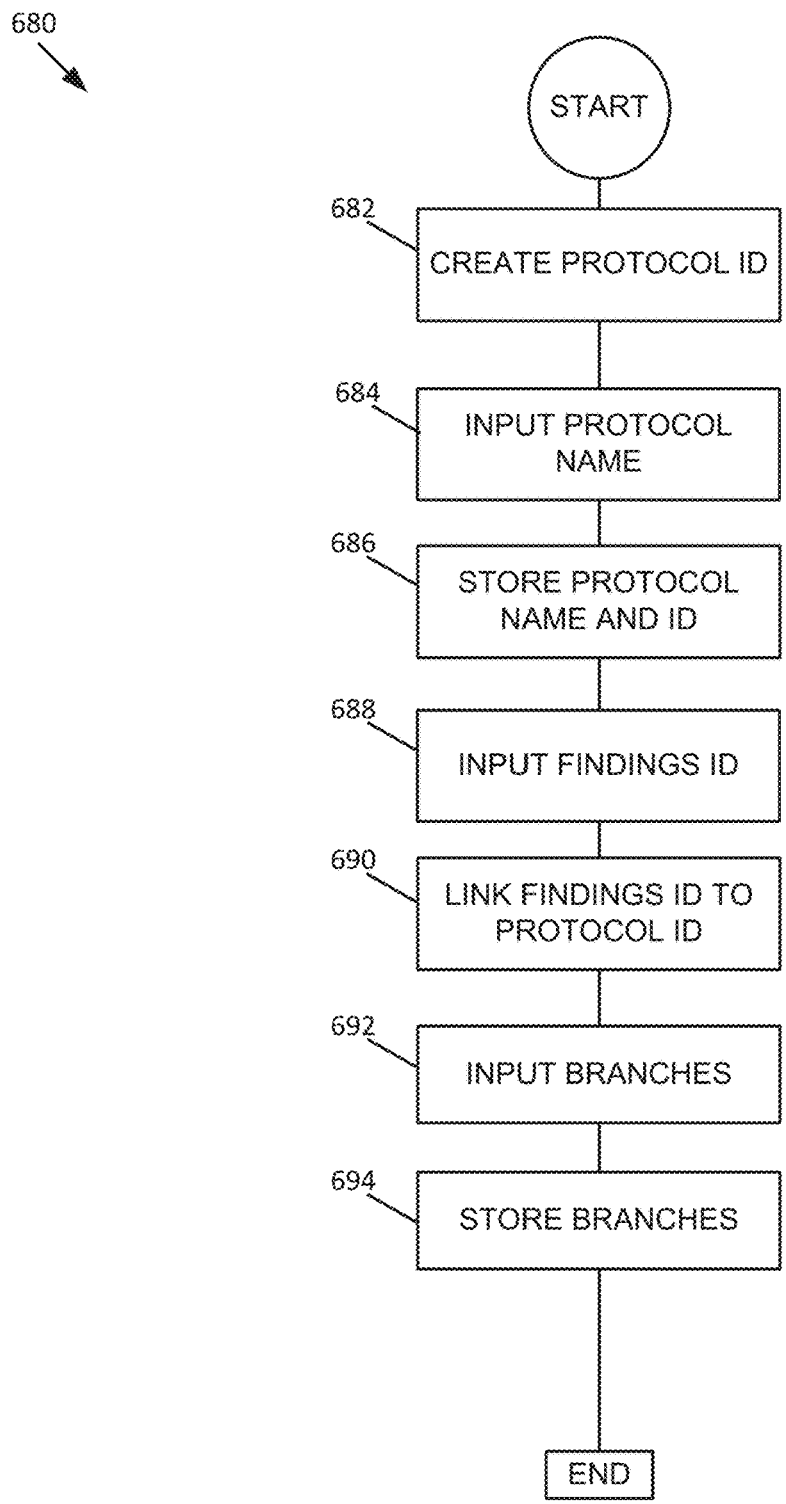
FIG. 12 is a flowchart of a method for creating a protocol.

At operation 516, the findings from the selected protocol or protocols are added to the note workspace 614 (shown in FIG. 12). In some embodiments, a template that is associated with one of the selected protocols is also applied to the note workspace 614 to modify the format or layout of the note workspace 614. If multiple protocols were selected and the protocols are associated with more than one template, the formatting information from the highest match protocol is applied. Other embodiments are possible as well. The protocols can be presented in any suitable user interface. An example of such an interface is the caregiver interface disclosed in U.S. Pat. No. 9,396,505, entitled CAREGIVER INTERFACE FOR ELECTRONIC MEDICAL RECORDS and issued on Jul. 19, 2016, the entire disclosure of which is incorporated herein. Other examples of interfaces are possible as well.

Figure 10:
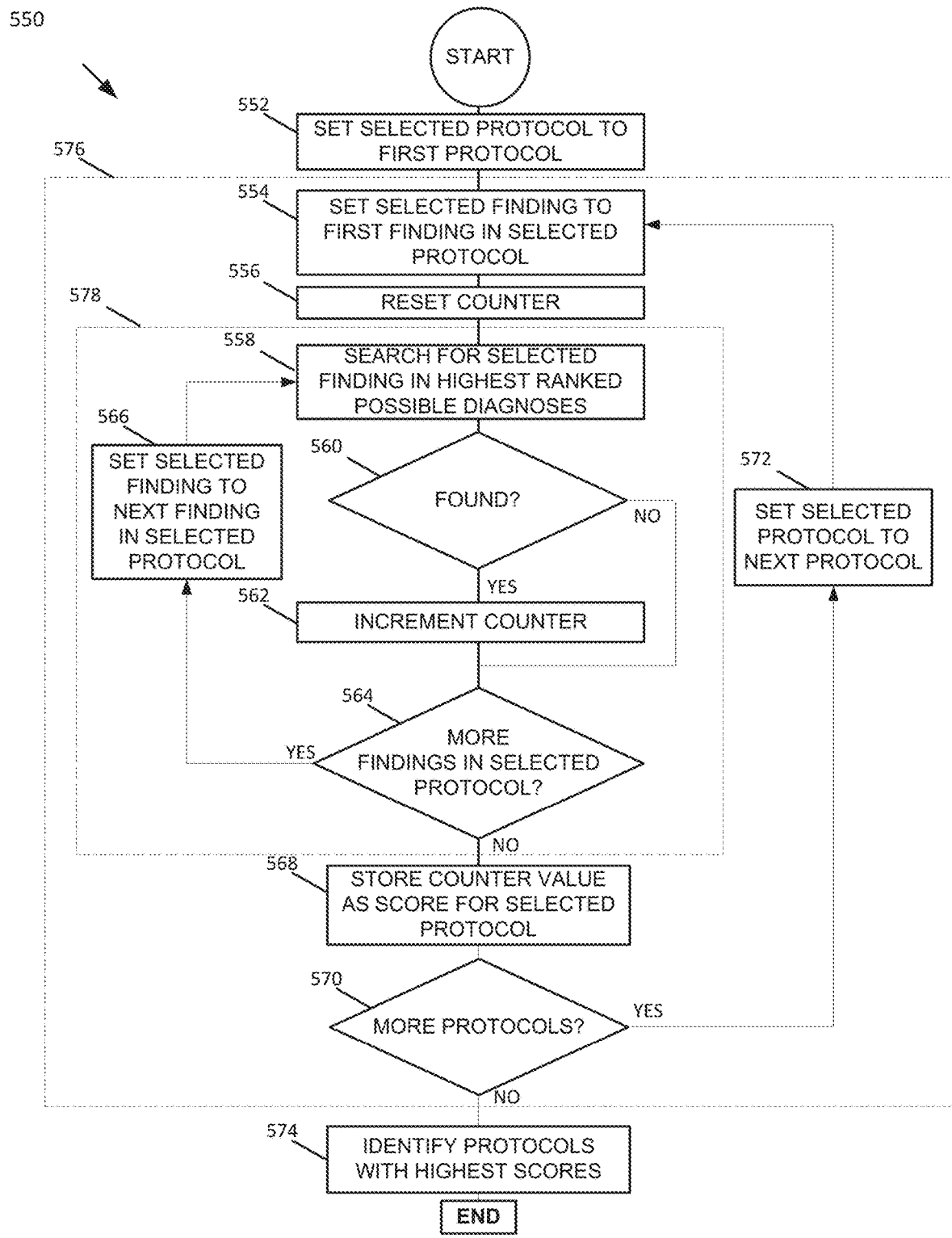
FIG. 10 is a flowchart of a method for identifying relevant protocols.

FIG. 10 is a flow chart illustrating an example method 550 of identifying relevant protocols. In some embodiments, the method 550 is performed by the protocol identification engine 194 using a processor (such as processing device 120, shown in FIG. 2). In this example, the method 550 includes operations 552, 554, 556, 558, 560, 562, 564, 566, 568, 570, 572, and 574.

In this example, the method 550 operates as two nested loops. The outer loop 576 comprises operations 554, 556, 558, 560, 562, 564, 566, 568, 570, and 572. The outer loop 576 iterates through each of the protocols. Each of the iterations of the outer loop 576 evaluates one of the protocols. Within the outer loop 576, the protocol that is being evaluated is referred to as the selected protocol.

The inner loop 578 comprises operations 558, 560, 562, 564, and 566. The inner loop 578 iterates through each finding in the selected protocol (i.e., the protocol being evaluated by the current iteration of the outer loop 576). Each of the iterations in the inner loop 578 evaluates one of the findings in the selected protocol. Within the inner loop 578, the finding that is being evaluated is referred to as the selected finding.

At operation 552, the selected protocol is set to the first protocol. This operation 552 serves to initialize the outer loop 576. In some embodiments, the first protocol is the first protocol stored in the protocol data 208. In other embodiments, the first protocol is the first protocol in a subset of the protocols stored in the protocol data 208. For example, in some embodiments, the subset of the protocols comprises only active protocols. Alternatively, or additionally, in some embodiments, the subset of the protocols comprises protocols that are relevant to the specialty of the caregiver C.

At operation 554, the selected finding is set to the first finding of the selected protocol. This operation 554 serves to, in part, initialize the inner loop 578.

At operation 556, a counter is reset to zero. The counter is used to count matches between findings in a protocol and findings in the highest ranked possible diagnoses. This operation 556 also serves to, in part, initialize the inner loop 578.

Within the inner loop 578, an operation 558 is performed to search for the selected finding in the highest ranked possible diagnoses. In some embodiments, this operation 558 is performed by iterating through each of the findings in each of the highest ranked possible diagnoses identified by operation 496 of method 490. In some embodiments, the selected finding is considered to be found only when the finding in the diagnosis is identical to the selected finding. This can be determined by comparing the finding IDs. In other embodiments, the selected findings are considered to be found when a related finding is found in the diagnosis. For example, in some embodiments, when the selected finding (from the selected protocol) is a child finding such as brassy cough and the diagnosis includes a parent of the child finding such as cough, the selected finding is considered to be found in the diagnosis. Other embodiments are possible as well.

At operation 560, it is determined whether the selected finding was found in one of the highest ranking possible diagnoses. If so, operation 562 is performed to increment the counter. If not, the operation 562 is skipped and the method 550 continues to operation 564. In some embodiments of operation 562, the counter is always incremented by one, which in effect weights each found finding equally.

An operation 564 is performed to determine whether there are more findings to evaluate in the selected protocol. If so, the operation 566 is performed to set the selected finding to the next finding in the selected protocol and then a new iteration of the inner loop 578 begins at operation 558. If not, the inner loop 578 is exited.

Returning back to the outer loop 576 now, an operation 568 is performed to store the value of the counter as the score for the currently selected protocol. In some embodiments, the score is stored in an array located in the memory 122 or in the secondary storage device 132. Other embodiments are possible as well.

An operation 570 is performed to determine whether there are more protocols to evaluate. If so, the operation 572 is performed to set the selected protocol to the next protocol and then a new iteration of the outer loop 576 begins with operation 554. If not, the outer loop 576 is exited.

At operation 574, the protocols with the highest score are identified as being potentially relevant. In some embodiments, operation 574 identifies a predetermined number of protocols having the highest scores. For example, in some embodiments, operation 574 identifies the 2-10 highest scoring protocols. Alternatively, in some embodiments, operation 574 identifies only the one highest scoring protocol. If there are two or more protocols sharing the highest score, operation 574 might identify each such protocol. Other embodiments that identify a different number of highest scoring protocols are possible as well. Additionally, in some embodiments, all protocols having a score that exceeds a predetermined threshold are identified as being potentially relevant. Other embodiments are possible as well.

Figure 11:
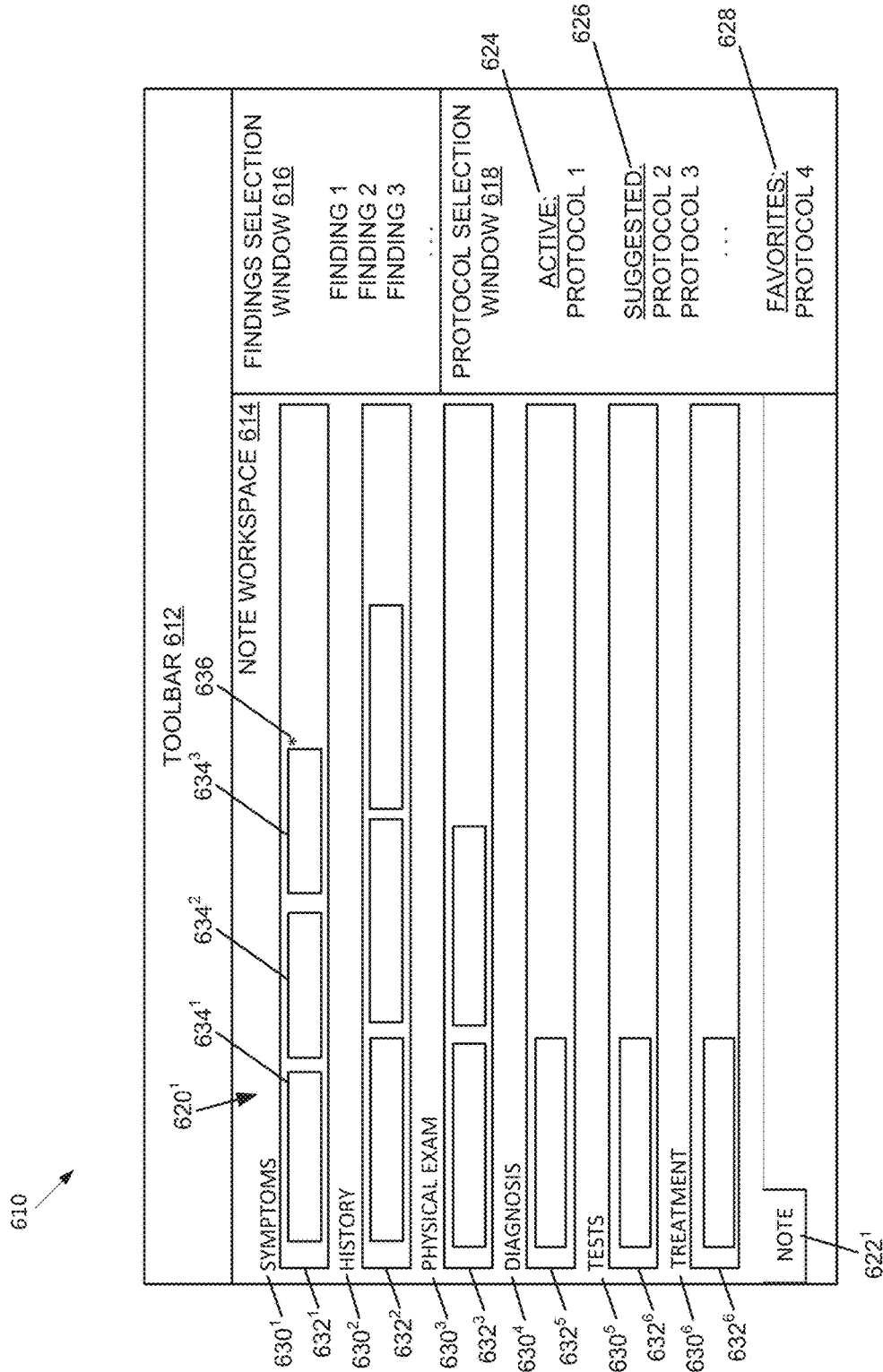
FIG. 11 is a block diagram illustrating a layout for a caregiver interface that can be generated by the user interface engine illustrated in FIG. 2.

FIG. 11 is a block diagram illustrating an example layout of the caregiver interface 118 as generated by the user interface engine 200. The caregiver interface 118 includes a toolbar 612, a note workspace 614, a template selection window 616, and a protocol selection window 618. The note workspace 614 includes one or more note data displays 620 and a selectable control 622 associated with each note data display 620.

The toolbar 612 provides a set of tools (not shown in FIG. 11) that are selectable by the caregiver C to initiate an associated function. In this example, the toolbar 612 is arranged along a top of the caregiver interface 118. In an example embodiment, the toolbar 612 includes tools, such as file management tools, protocol or template administration tools, patient selection tools, formatting tools, dictation tools, and administrative tools. Other embodiments include more or fewer tools. Some embodiments do not include the toolbar 612. In some embodiments, the toolbar 612 is located in a different part of the caregiver interface 118, and can be arranged in a separate or expandable window, if desired.

In an example embodiment, the note workspace 614 is a window that presents one or more note data displays 620 to the caregiver C. The note data displays 620 include a current note data display $620^1$ (where the caregiver C can record findings of a current interaction or encounter). The current note data display $620^1$ operates to display findings stored in the encounter data 210 (shown in FIG. 3) as well as to display new findings as they are entered by the caregiver C.

In some embodiments, the note data display templates include a layout that defines the organization and visual arrangement of data, a plurality of finding categories 630, and associated input fields 652 where findings from the current interaction can be recorded in the current note data display $620^1$. In the example shown in FIG. 11, the findings category $630^1$ represents symptoms and includes the associated group $632^1$ of input fields. The group $632^1$ of input fields includes the findings $634^1$, $634^2$, and $634^3$. The example shown also includes a visual indicator 636, adjacent to finding $634^3$ that indicates that $634^3$ is part of the active protocol. In this manner, the caregiver C can quickly discern which findings are specified by the active protocol or protocols.

As new findings are entered by the caregiver C, the new findings are also stored in the encounter data 210. In some embodiments, the note data displays 620 also include one or more historical note data displays (not shown in FIG. 11), which are associated with a historical record for the patient P and display the findings from a prior interaction or encounter between the caregiver C (or another caregiver) and the patient P.

Each note data display 620 is linked to a selectable control 662. When the selectable control 662 is selected by the caregiver C, the user interface engine 200 updates the caregiver interface 118 to display the note data display 620 in the workspace 614 that is linked to the selected selectable control 662. An example of the selectable control 662 is a tab, as shown in FIG. 11. Other embodiments include other selectable controls, such as a button, link, icon, dropdown menu, selectable list, check box, etc.

In some embodiments, when a new patient interaction begins, the caregiver interface 118 is generated, and includes a blank current note data display $620^1$. To begin making a record of the interaction, the caregiver C can enter medical findings for the chief complaint or initial assessment. In some embodiments, the caregiver C inputs these findings using one or more of the keyboard 146, the mouse 148, the microphone 150, or the touch sensor 152 (all shown in FIG. 2). In some embodiments, the caregiver C enters these findings as freeform speech or text entries. Other embodiments are possible as well.

The findings selection window 616 includes a list of findings that a caregiver C may add to the current note data display $620^1$. In some embodiments, the caregiver C enters some or all findings by making selections from the list of findings in the findings selection window 616. Initially, in some embodiments, the findings listed in the findings selection window 616 include commonly used findings. Additionally, in some embodiments, the findings listed in the findings selection window 616 are generated by the intelligent prompting engine 192 (shown in FIG. 3).

In this example, the protocol selection window 618 includes an active list 624 of active protocols, a suggested list 626 of suggested protocols, and a favorites list 628 of favorite protocols. When a protocol is selected from the protocol selection window 618, the medical findings associated with the protocol are added to the current note data display $620^1$. In some embodiments, the caregiver C selects one or more protocols from the protocol selection window 618 to start entering findings for the patient P.

The active list 624 includes the protocols that have been previously added to the current note data display $620^1$. In some embodiments, the caregiver C can choose to remove a protocol listed in the active list 624, such as by right clicking on it and choosing a remove option from a pop-up menu (not shown in FIG. 11).

The suggested list 626 includes protocols identified by the intelligent prompting engine 192 (shown in FIG. 3). In some embodiments, the protocols listed in the suggested list 626 are updated when the caregiver C sends a command to the user interface engine 200 (shown in FIG. 3), such as by clicking on a button. In other embodiments, the protocols listed in the suggested list 626 are updated each time a finding is added to the current note data display $620^1$.

Some embodiments include a favorites list 628. The favorites list 628 displays a list of the caregiver's most frequently used, or "favorite," protocol. In some embodiments, the caregiver C customizes the protocols shown in the favorites list 628. Additionally, in some embodiments, the favorites are determined otherwise.

FIG. 12 is a flow chart illustrating an example method 680 of creating a protocol. In some embodiments, the method 680 is performed by the protocol administration engine 198 using a processor (such as processing device 120, shown in FIG. 2). In this example, the method 680 includes operations 682, 684, 686, 688, 690, 692, 694, and 696.

At operation 682, a protocol ID is created. In some embodiments, the protocol ID is a unique key for the protocol data table 250 (shown in FIG. 4).

At operation 684, the name of the protocol is input by the caregiver C or an administrator. The name of the protocol is received by the protocol administration engine 198. In some embodiments, the protocol name is a short name that can be quickly recognized by a caregiver C. In addition, in some embodiments, additional information is input as well, such as instructions for using the protocol.

At operation 686, the protocol name and ID are stored. In some embodiments, the protocol name and ID are stored in the data center 108 using the data center interface engine 190.

At operation 688, the finding IDs for findings that will be associated with the protocol are input. In some embodiments, the finding IDs are a unique key for the medical findings data table 252 (shown in FIG. 4). In some embodiments, the finding IDs are selected from a list of medical findings by the caregiver C or and administrator. Additionally, in some embodiments, the intelligent prompting engine 192 suggests findings to include in the protocol. In some embodiments, the protocol administration engine 198 receives the finding IDs.

At operation 690, the finding IDs inputted in operation 688 are linked to the protocol ID created in operation 682. In some embodiments, this finding ID is linked to the protocol ID by adding a record to the protocol-finding relationship table 256. Additionally, in some embodiments, information about branching (e.g., branch conditions and branch protocols) are also input and stored in the protocol-finding relationship table 256.

At operation 692, branches are input. In some embodiments, the branches specify a one or more finding IDs and conditions that are utilized to indicate that the protocol branches. In some embodiments, the branch specifies additional findings or another protocol to incorporate if the branch condition is met. Other embodiments are possible. The branches are input by a caregiver C or administrator and are received by the protocol administration engine 198.

At operation 694, the branches are stored in the protocol data 208. In some embodiments, the branches are stored in the branches table 254 and linked in the protocol-finding relationship table 256. Other embodiments are possible however.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A method of generating a user interface for use in documenting a patient encounter, the method comprising:
    identifying at least one medical finding;
    automatically identifying, with a computing device, two or more documentation protocols based on the at least one medical finding;
    merging the identified document protocols; and
    automatically generating a user interface including the merged documentation protocols, the merged documentation protocols corresponding to the identified at least one medical finding, and at least one of the identified document protocols having a score equal to or greater than a determined value.

2. The method of claim 1 wherein each score assigned to a documentation protocol identified in the act of identifying documentation protocols is based the number of medical findings identified by the medical finding data entered through the user interface that are linked to the documentation protocol in the database.

3. The method of claim 2 further comprising:
    displaying on the user interface the documentation protocol having the highest score.

4. The method of claim 1 wherein the user interface displays the medical findings for each identified documentation protocol, the method further comprising:
    upon identifying two or more documentation protocols, merging the identified documentation protocols;
    filtering duplicate medical findings from the merged documentation protocols; and
    displaying the documentation protocol, the displayed documentation protocol comprising only one entry for a medical finding linked to two or more of the merged documentation protocols.

5. The method of claim 1 wherein the predetermined score is the highest score assigned to the identified documentation protocols.

6. The method of claim 1 wherein the processor is programmed to:
    upon identifying two or more documentation protocols, merge the identified documentation protocols;
    filter duplicate medical findings from the merged documentation protocols; and
    display the documentation protocol in the user interface, the displayed documentation protocol comprising only one entry for a medical finding linked to two or more of the merged documentation protocols.

7. An apparatus for generating a user interface for use in documenting a patient encounter, the apparatus comprising:
    a processor in data communication with a memory and a display; and
    the processor programmed to identify at least one medical finding, automatically identify two or more documentation protocols based on the at least one medical finding, merging the identified document protocols, and automatically generate a user interface including the merged documentation protocols, the documentation protocols corresponding to the identified at least one medical finding, at least one of the identified documentation protocols having a score equal to or greater than a determined value.

8. The apparatus of claim 7 wherein the memory is located remotely from the processor.

9. The apparatus of claim 7 further comprising a display in data communication with the processor, and wherein the display displays the user interface.

10. The apparatus of claim 9 wherein the processor and display form a single computing device.

11. The apparatus of claim 9 wherein the processor is programmed to display the protocol having the highest score in the user interface.

12. The apparatus of claim 7 wherein the predetermined score is the highest score assigned to the identified documentation protocols.

* * * * *